US007012146B2

(12) United States Patent
Jensen et al.

(10) Patent No.: US 7,012,146 B2
(45) Date of Patent: Mar. 14, 2006

(54) ION CHANNEL MODULATING AGENTS

(75) Inventors: Bo Skaaning Jensen, Copenhagen (DK); Dorte Strobaek, Farum (DK); Palle Christophersen, Ballerup (DK); Lene Teuber, Vaerlose (DK); Jurgen Beyer, Copenhagen (DK)

(73) Assignee: Poseidon Pharmaceuticals A/S, Ballerup (DK)

( * ) Notice: Subject to any disclaimer, the term of this patent is extended or adjusted under 35 U.S.C. 154(b) by 0 days.

(21) Appl. No.: 09/854,694

(22) Filed: May 15, 2001

(65) Prior Publication Data
US 2002/0169203 A1 Nov. 14, 2002

Related U.S. Application Data

(63) Continuation of application No. PCT/DK99/00731, filed on Dec. 22, 1999.

(30) Foreign Application Priority Data

Dec. 22, 1998 (DK) ............................... 1998 01722
Mar. 23, 1999 (DK) ............................... 1999 00403
May 12, 1999 (DK) ............................... 1999 00660

(51) Int. Cl.
C07D 213/02 (2006.01)
(52) U.S. Cl. ............................................ 546/342
(58) Field of Classification Search ................ 546/329, 546/342; 514/357
See application file for complete search history.

(56) References Cited

U.S. PATENT DOCUMENTS 3,268,540 A * 8/1966 Mohrbacher ................. 546/183
6,204,277 B1 * 3/2001 Shinkai et al. ............... 514/374

FOREIGN PATENT DOCUMENTS

EP 228192 * 1/1986
WO 9806720 * 2/1998

OTHER PUBLICATIONS

Umemoto et al., "Power and Structure—Variable Fluorinating Agents. The N-Fluropyridinium Salt System", J. Am. Chem. Soc. 1990, 112, 8563-8575.*

Sammes et al., Synthetic Applications of N—N Linked Heterocyclies. Part 16. Reactions between Carbanions Derived from arbon Acid with pKa 7-14 and N-(2,6-dimethyl-4-oxopyridin-1-yl)pyridinium Tetrafluoroborate: Synthesis of 4-substituted pyridines, an.*
Gargus, et al., "Unraveling Monogenic Channelopathies and Their Implications for Complex Polygenic Disease", Am. J. Hum. Genet., 72:785-803, 2003.*
Merlo et al., "Modifier genes in cystic fibrosis lung disease", Journal of Laboratory and Clinical Medicine (2003), 141 (4), 237-241.*
CA 128:204878 , "Preparation of pyrazinobenzothiazine derivatives and analogs fro the treatement of inflammation and autoimmune diseases", Kaneko et al. cont. Observatin of Pyridine Ring-opening Reactions, p. 2835-2839.*
Laohachai et. al., "The role of bacterial and non-bacterial toxins in the induction of changes in membrane transport: implications for diarrhea", pp. 687-707.*
Smerz et. al., "Nickel-Catalyzed Hydroxylation of 1,3-Dicarbonyl Compounds by Dimethyldioxirane", Tetrahedron, vol. 52, No. 16, 5799-5804.*
Miyoshi et al, Journal of Biological Chemistry, vol. 273, No. 28, pp. 17368-17374, 1998.*
Andrako et al., J. Pharm. Sci., vol. 50, pp. 337-340 (1961).
Zymalkowski, Arch. Pharm., vol. 291, pp. 436-442 (1958).
Porter et al., Int. J. Peptide Protein Res. vol. 30, pp. 13-21 (1987).
Kawabata et al., Liebigs Ann. Chem., (1990) pp. 181-183.
Aldrich Catalog Handbook of Fine Chemicals, 1996-1997, pp. 510-525, 264-266, 268, 277, 278, 324, 385, 518, 563, 580, 597, 602, 622, 627, 997, 1010, 1064, 1458, and 1480.

* cited by examiner

Primary Examiner—Zinna Northington Davis
(74) Attorney, Agent, or Firm—Birch, Stewart, Kolasch & Birch, LLP

(57) ABSTRACT

The present invention relates to ion channel modulating agents. More particularly, the present invention relates to a particular class of chemical compounds that has proven useful as modulators of SK Ca, IK Ca and BK Ca channels. In further aspects, the present invention relates to the use of these SK/IK/BK channel modulating agents for the manufacture of medicaments, for methods of therapy, and pharmaceutical compositions comprising the SK/IK/BK channel modulating agents. The SK/IK/BK channel modulating agents of the invention are useful for the treatment or alleviation of diseases and conditions associated with the SK/IK/BK channels.

7 Claims, No Drawings

ION CHANNEL MODULATING AGENTS

This application is a Continuation of PCT International Application No. PCT/DK99/00731 filed on Dec. 22, 1999, which was published in English and which designated the United States and on which priority is claimed under 35 U.S.C. § 120, the entire contents of which are hereby incorporated by reference.

TECHNICAL FIELD

The present invention relates to ion channel modulating agents. More particularly, the present invention relates to a particular class of chemical compounds that has proven useful as modulators of $SK_{Ca}$, $IK_{Ca}$ and $BK_{Ca}$ channels. In further aspects, the present invention relates to the use of these SK/IK/BK channel modulating agents for the manufacture of medicaments, for methods of therapy, and pharmaceutical compositions comprising the SK/IK/BK channel modulating agents.

The SK/IK/BK channel modulating agents of the invention are useful for the treatment or alleviation of diseases and conditions associated with the SK/IK/BK channels.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

Many drugs exert their effects via modulation of ion channels. Examples are anti-epileptic compounds like Phenytoin and Lamotrigine, which block voltage dependent $Na^+$-channels in the brain, anti-hypertensive drugs like Nifedipine and Diltiazem, which block voltage dependent $Ca^{2+}$-channels in smooth muscle cells, and stimulators of insulin release like Glibenclamide and Tolbutamide, which block an ATP-regulated $K^+$-channel in the pancreas.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_V$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

$Ca^{2+}$-activated SK channels are present in many central neurons and ganglia, where their primary function is to hyperpolarize nerve cells following one or several action potentials to prevent long trains of epileptogenic activity to occur. The SK channels are also present in several peripheral cells including skeletal muscle, gland cells, liver cells, and T-lymphocytes.

The significance of SK channels in normal skeletal muscle is not clear, but their number is significantly increased in denervated muscle, and the large number of SK channels in the muscle of patients with myotonic muscle dystrophia suggest a role in the pathogenesis of the disease.

A number of blockers of SK channels exist, e.g. apamin, atracurium, pancuronium, and tubocurarine, and they are all positively charged molecules which act as pore blockers.

The $Ca^{2+}$-activated IK channel shares a number of characteristics with the $Ca^{2+}$-activated SK channel, since it is highly K-selective, is activated by sub-micromolar concentrations of $Ca^{2+}$, and has an inwardly rectifying conductance. However, there are also striking differences. The unit conductance of the IK channel is 4–5 fold higher than that of the SK channel, and the distribution of the IK channel is restricted to the blood and vasculature. Thus, the IK channel is not expressed in the nervous system and in muscle, but in endothelial cells, cells of epithelial origin and in red blood cells.

In the red blood cells, where the IK channel has been denominated the Gardos channel, a rise in the concentration of intracellular $Ca^{2+}$ opens the channel and causes potassium loss and cell dehydration, a condition which is exacerbated in sickle cell anemia. Promising therapeutic approaches for sickle cell anemia involve specific block of the IK channel.

IK channels have also been implicated in the microvasculature of the kidney, where they may be responsible for the vasodilatory effects of bradykinin. The decrease in blood pressure during septic shock is caused by an increased NO production by the endothelial cells, and the IK channels in these cells are responsible for maintaining the $Ca^{2+}$ influx activating the $Ca^{2+}$-sensitive NO-synthase.

In brain capillary endothelial cells, IK channels, activated by endothelin that is produced by neurons and glia, shunt excess $K^+$ into the blood. Neurotrophilic granulocytes, i.e. mobile phagocytic cells that defend the body against microbial invaders, undergo large depolarisation subsequent to agonistic stimulation, and IK channels have been implicated in depolarising the stimulated granulocyte.

The $Ca^{2+}$-activated BK channels present in many cells including most central and peripheral nerve cells, striated muscle cells, cardiac cells, smooth muscle cells of the airways, the vasculature, the gastrointestinal tract and bladder, in endo- and exocrine glands including pancreatic b-cells and in kidney tubules.

SUMMARY OF THE INVENTION

According to the present invention it has now been found that a particular group of chemical compounds possess valuable activity as modulators of $SK_{Ca}$, $IK_{Ca}$ and/or $BK_{Ca}$ channels.

In its first aspect the invention relates to novel chemical compounds represented by the general formula I

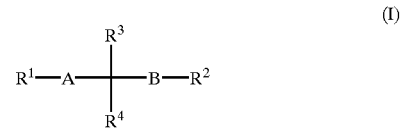

wherein

A and B, independently of each another represent a group of the formula —$(CH_2)_n$—, of the formula —$(CH_2)_n$—Y— (in either direction), or of the formula —$(CH_2)_n$—Y—$(CH_2)_m$—;

in which formulae n and m, independently of each another, represent 0, 1, 2, 3 or 4, and Y represents O, S, or NR''', wherein R''' represents hydrogen or alkyl;

$R^1$ and $R^2$, independently of each another, represent alkyl, alkenyl, alkynyl, cycloalkyl, amino, trihalogenmethyl, nitro, cyano, or phenyl, or a group of the formula —OR', —SR', —R'OR'', —R'SR'', —C(O)R', —C(S)R', —C(O)OR', —C(S)OR', —C(O)SR', —C(S)SR', —C(O)NR'(OR''), —C(S)NR'(OR''), —C(O)NR'(SR''), —C(S)NR'(SR''), —CH(CN)$_2$, —C(O)NR'R'', —C(S)NR'R'', —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, CH$_2$OR', CH$_2$SR', —NR'C(O)R'', or —OC(O)R'; an unsaturated or a partially or completely saturated mono- or polycyclic group, a mono- or poly-heterocyclic group, an aralkyl group, or a hetero-alkyl group, which mono- or polycyclic groups or aralkyl or hetero-alkyl groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR';

wherein R' and R'', independently of each another, represent hydrogen, alkyl, alkenyl, alkynyl, cycloalkyl or alkoxy, or a group of the formula NR'''R'''', wherein R''' and R'''', independently of each another, represent hydrogen or alkyl;

$R^3$ and $R^4$, independently of each another, represent alkyl, alkenyl, alkynyl, cycloalkyl, amino, trihalogenmethyl, nitro, cyano, or phenyl, or a group of the formula —OR', —SR', —R'OR'', —R'SR'', —C(O)R', —C(S)R', —C(O)OR', —C(S)OR', —C(O)SR', —C(S)SR', —C(O)NR'(OR''), —C(S)NR'(OR''), —C(O)NR'(SR''), —C(S)NR'(SR''), —CH(CN)$_2$, —C(O)NR'R'', —C(S)NR'R'', —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, CH$_2$OR', CH$_2$SR', —NR'C(O)R'', or —OC(O)R';

wherein R' and R'', independently of each another, represent hydrogen, alkyl, alkenyl, alkynyl, cycloalkyl or alkoxy, or a group of the formula NR'''R'''', wherein R''' and R'''', independently of each another, represent hydrogen or alkyl;

or $R^3$ and $R^4$ together form an unsaturated or a partially or completely saturated mono- or polycyclic group, or a mono- or poly-heterocyclic group, which mono- or polycyclic groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR';

wherein R' and R'', independently of each another, represent hydrogen, alkyl, alkenyl, alkynyl, cycloalkyl or alkoxy, or a group of the formula NR'''R'''', wherein R''' and R'''', independently of each another, represent hydrogen or alkyl.

In a second aspect, the invention provides a pharmaceutical composition comprising a chemical compound of the invention for the treatment or alleviation of diseases or conditions responsive to modulation of $SK_{Ca}$, $IK_{Ca}$ and/or $BK_{Ca}$ channels.

The SK/IK/BK channel modulating agents of the invention are useful for the treatment or alleviation of diseases or conditions responsive to modulation of $SK_{Ca}$, $IK_{Ca}$ and/or $BK_{Ca}$ channels.

DETAILED DISCLOSURE OF THE INVENTION

According to the present invention it has now been found that a particular group of chemical compounds possess valuable activity as modulators of $Sk_{Ca}$, $IK_{Ca}$ and/or $BK_{Ca}$ channels.

SK/IK/BK Modulating Agents

In the context of this invention, chemical compounds capable of affecting $Sk_{Ca}$, $IK_{Ca}$ and/or $BK_{Ca}$ channels are designated SK/IK/BK channel modulating agents. The SK/IK/BK channel modulating agents of the invention may affect the ion channels by opening (activating) the channels or by inhibiting (blocking) the channels.

The SK/IK/BK channel modulating agents of the invention are represented by the following general formula I

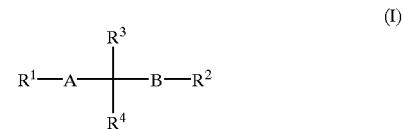

(I)

and a pharmaceutically acceptable salt or an oxide or a hydrate thereof, wherein, A and B, independently of each another represent a group of the formula —(CH$_2$)$_n$—, of the formula —(CH$_2$)$_n$—Y— (in either direction), or of the formula —(CH$_2$)$_n$—Y—(CH)$_m$—;

in which formulae n and m, independently of each another, represent 0, 1, 2, 3 or 4, and Y represents O, S, or NR''', wherein R''' represents hydrogen or alkyl;

$R^1$ and $R^2$, independently of each another, represent alkyl, alkenyl, alkynyl, cycloalkyl, amino, trihalogenmethyl, nitro, cyano, or phenyl, or a group of the formula —OR', —SR', —R'OR'', —R'SR'', —C(O)R', —C(S)R', —C(O)OR', —C(S)OR', —C(O)SR', —C(S)SR'; —C(O)NR'(OR''), —C(S)NR'(OR''), —C(O)NR'(SR''), —C(S)NR'(SR''), —CH(CN)$_2$, —C(O)NR'R'', —C(S)NR'R'', —CH[C(O)R']$_2$, —CH[C(S)R']$_2$, —CH[C(O)OR']$_2$, —CH[C(S)OR']$_2$, —CH[C(O)SR']$_2$, —CH[C(S)SR]$_2$,CH$_2$OR', CH$_2$SR', —NR'C(O)R'', or —OC(O)R';

an unsaturated or a partially or completely saturated mono- or polycyclic group, a mono- or poly-heterocyclic group, an aralkyl group, or a hetero-alkyl group, which mono- or polycyclic groups or aralkyl or hetero-alkyl groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR';

wherein R' and R", independently of each another, represent hydrogen, alkyl, alkenyl, alkynyl, cycloalkyl or alkoxy, or a group of the formula NR'''R"", wherein R''' and R"", independently of each another, represent hydrogen or alkyl;

$R^3$ and $R^4$, independently of each another, represent alkyl, alkenyl, alkynyl, cycloalkyl, amino, trihalogenmethyl, nitro, cyano, or phenyl, or a group of the formula —OR', —SR', —R'OR", —R'SR", —C(O)R', —C(S)R', —C(O)OR', —C(S)OR', —C(O)SR', —C(S)SR', —C(O)NR'(OR"), —C(S)NR'(OR"), —C(O)NR'(SR"), —C(S)NR'(SR"), —CH(CN)$_2$, —C(O)NR'R", —C(S)NR'R", —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, CH$_2$OR', or CH$_2$SR', —NR'C(O)R", or —OC(O)R';

wherein R' and R", independently of each another, represent hydrogen, alkyl, alkenyl, alkynyl, cycloalkyl or alkoxy, or a group of the formula NR'''R"", wherein R''' and R"", independently of each another, represent hydrogen or alkyl;

or $R^3$ and $R^4$ together form an unsaturated or a partially or completely saturated mono- or polycyclic group, or a mono- or poly-heterocyclic group, which mono- or polycyclic groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR';

wherein R' and R", independently of each another, represent hydrogen, alkyl, alkenyl, alkynyl, cycloalkyl or alkoxy, or a group of the formula NR'''R"", wherein R''' and R"", independently of each another, represent hydrogen or alkyl.

In a preferred embodiment, the chemical compound of the invention is a malonic acid ester derivative of general formula II

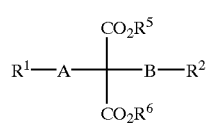

(II)

and a pharmaceutically acceptable salt or an oxide or a hydrate thereof, wherein, A, B, $R^1$ and $R^2$ are as defined above; and $R^5$ and $R^6$, independently of each another, represent hydrogen, alkyl, cycloalkyl, or a group of the formula NR'''R"", wherein R''' and R"", independently of each another, represent hydrogen or alkyl.

In another preferred embodiment, the chemical compound of the invention is a malonic acid ester derivative as described above, in which $R^5$ and $R^6$ together form a heterocyclic 6-9 membered ring to give a diester derivative of the general formula III

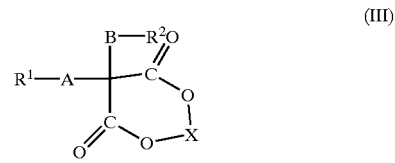

(III)

and a pharmaceutically acceptable salt or an oxide or a hydrate thereof, wherein, A, B, $R^1$ and $R^2$ are as defined above; and X represents a saturated or unsaturated carbon chain of the formula —(CH$_2$)$_n$—, wherein n is 1, 2, 3 or 4; of the formula —CH$_2$—CH═CH—CH$_2$—; of the formula —CH═CH—CH$_2$—CH$_2$— (in either direction); or of the formula —CH$_2$—C≡C—CH$_2$—.

In a third preferred embodiment, the chemical compound of the invention is an oxo derivative of the general formula IV

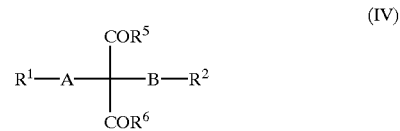

(IV)

and a pharmaceutically acceptable salt or an oxide or a hydrate thereof, wherein, A, B, $R^1$ and $R^2$ are as defined above; and $R^5$ and $R^6$, independently of each another, represent hydrogen, alkyl, cycloalkyl, or a group of the formula NR'''R"", wherein R''' and R"", independently of each another, represent hydrogen or alkyl.

In a fourth preferred embodiment, the chemical compound of the invention is an ether derivative of the general formula V

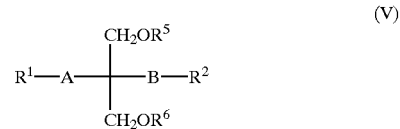

(V)

and a pharmaceutically acceptable salt or an oxide or a hydrate thereof, wherein, A, B, $R^1$ and $R^2$ are as defined above; and $R^5$ and $R^6$, independently of each another, represent hydrogen, alkyl, cycloalkyl, or a group of the formula NR'''R"", wherein R''' and R"", independently of each another, represent hydrogen or alkyl.

In a more preferred embodiment, the chemical compound of the invention is a chemical compound as defined above, wherein $R^1$ and $R^2$ independently of each another represents an alkyl group; a phenyl or a benzyl group, which phenyl and benzyl groups may optionally be substituted one or more times with substituent selected from the group consisting of halogen, $CF_3$, CN, amino or nitro; a mono-heterocyclic group, which heterocyclic group may optionally be substituted one or more times with substituent selected from the group consisting of halogen, $CF_3$, CN, amino or nitro; a heteroalkyl group, wherein the heterocyclic group a mono-heterocyclic group, which heterocyclic group may optionally be substituted one or more times with substituent selected from the group consisting of halogen, $CF_3$, CN, amino or nitro.

In another preferred embodiment, the chemical compound of the invention is a chemical compound as defined above, wherein $R^1$ and $R^2$ independently of each another represents phenyl, 1-, 2 or 3-chlorophenyl, 1-, 2- or 3-chlorobenzyl, 1-, 2- or 3-nitrophenyl, 1-, 2- or 3-nitrobenzyl, 1-, 2 or 3-trifluoromethylphenyl, 1-, 2- or 3-trifluoromethylbenzyl or 1-nitro-3-trifluoromethyl-5-chlorophenyl, 1-nitro-3-trifluoromethyl-5-chlorobenzyl.

In a third preferred embodiment, the chemical compound of the invention is a chemical compound as defined above, wherein mono-heterocyclic group is an aromatic heterocyclic monocyclic group, in particular 1,3,2,4- or 1,3,4,5-dioxadiazolyl, dioxatriazinyl, dioxazinyl, 1,2,3-, 1,2,4-, 1,3,2- or 1,3,4-dioxazolyl, 1,3,2,4- or 1,3,4,5-dithiadiazolyl, dithiatriazinyl, dithiazinyl, 1,2,3-dithiazolyl, furanyl, furazanyl, imidazolyl, isoimidazolyl, 2-isoimidazolyl, isoindazolyl, isothiazolyl, isoxazolyl, 1,2,3-, 1,2,4-, 1,2,5- or 1,3,4-oxadiazolyl, oxatetrazinyl, oxatriazinyl, 1,2,3,4- or 1,2,3,5-oxatriazolyl, oxazolyl, pyrazinyl, pyrazolyl, pyridazinyl, pyridinyl, pyrimidinyl, pyrrolyl (azolyl), 1,2,3,4- or 2,1,3,4-tetrazolyl, thiadiazolyl, thiazolyl, thienyl, 1,2,3-, 1,2,4- or 1,3,5-triazinyl, or 1,2,3-, 1,2,4-, 2,1,3- or 4,1,2-triazolyl.

In a fourth preferred embodiment, the chemical compound of the invention is a chemical compound as defined above, wherein the mono-heterocyclic group is 2-furanyl, 3-furanyl, 2-, 4- or 5-imidazolyl, 3-, 4- or 5-isoxazolyl, 1-, 2- or 3-pyridinyl, or 1- or 2-thienyl.

In a fifth preferred embodiment, the chemical compound of the invention is a chemical compound as defined above, wherein the mono-heterocyclic group is 4-(3,5-dimethyl)-isoxazolyl.

In a sixth preferred embodiment, the chemical compound of the invention is a chemical compound as defined above, wherein the mono-heterocyclic group is an unsaturated or a partially or completely saturated heterocyclic monocyclic group, in particular 1,3,5,6,2-dioxadiazinyl, 1,2,3,4,5-, 1,2,3,5,4-dioxadiazolyl, dioxanyl, 1,3-dioxolyl, 1,3,5,6,2-dithiadiazinyl, 1,2,3,4,5- or 1,2,3,5,4-dithiadiazolyl, 2-isoimidazolyl, isopyrrolyl, isotetrazolyl, 1,2,3- or 1,2,4-isotriazolyl, morpholinyl, oxadiazinyl, 1,2,4-, 1,2,6-, 1,3,2-, 1,3,6- or 1,4,2-oxazinyl, piperazinyl, piperidinyl, 1,2-, 1,3- or 1,4-pyranyl, or pyrrolidinyl.

In a seventh preferred embodiment, the chemical compound of the invention is a chemical compound as defined above, wherein the mono-heterocyclic group is an aromatic heterocyclic polycyclic group, in particular acridinyl, benzimidazolyl, 1,2- or 1,4-benzisothiazinyl, 1,2- or 1,4-benzisoxazinyl, benzisoxazole, benzothiazolyl, benzofuranyl, isobenzofuranyl, 2,3-benzopyronyl, 1,2,3,4-benzotetrazinyl, 1,3,4,6-benzotetrazolyl, benzothiazolyl, 1,2,3- or 1,2,4-benzotriazinyl, 1,2,3- or 2,1,3-benzotriazolyl, benzoxadiazolyl, benzoxazolyl, carbazolyl, cinnolinyl, coumarinyl, indazolyl, indolyl, isoindolyl, indolizinyl, purinyl, phenazinyl, phenothiazinyl, phenanthridinyl, phthalazinyl, pteridinyl, quinolinyl, quinoxalinyl, isoquinolinyl, quinazolinyl, quinolizinyl, or xanthrenyl.

In an eight preferred embodiment, the chemical compound of the invention is a chemical compound as defined above, wherein the mono-heterocyclic group is an unsaturated or a partially or completely saturated heterocyclic polycyclic group, in particular 1,3-benzisodiazolyl, benzomorpholinyl, 1,2- or 1,4-benzopyranyl, 1,3,2-, 1,4,2-, 2,3,1- or 3,1,4-benzoxazinyl, chromanyl, 4H-chromenyl, or indanyl.

In a ninth preferred embodiment, the chemical compound of the invention is a chemical compound as defined above, wherein the heteroalkyl group is furfuryl, or picolyl.

In a most preferred embodiment, the chemical compound of the invention is

Diethyl 2-(4-fluorophenyl)-2-(3-picolyl)malonate;

Diethyl 2-(4-nitrophenyl)-2-(2-picolyl)malonate;

Diethyl 2-(4-nitrophenyl)-2-(4-picolyl)malonate;

Diethyl 2-phenyl-2-(3-picolyl)malonate;

Diethyl 2-(5-chloro-2-nitro-4-(trifluoromethyl)phenyl)-2-(3-picolyl)malonate;

Diethyl 2-benzyl-2-(3-picolyl)malonate;

Diethyl 2-(4-nitrophenyl)-2-[(benzotriazol-1-yl)methyl]malonate;

Diethyl 2-(2-thienyl)-2-(2-picolyl)malonate;

Diethyl 2-(4-(acetylamino)phenyl)-2-(2-picolyl)malonate;

Diethyl 2-(4-(benzoylamino)phenyl)-2-(2-picolyl)malonate; or 2-(4-nitrophenyl)-2-(2-picolyl)malononitril;

or a pharmaceutically acceptable salt or an oxide or a hydrate thereof.

In another embodiment, the chemical compound of the invention is a represented by the general formula VI

and a pharmaceutically acceptable salt or an oxide or a hydrate thereof, wherein, $R^1$ and $R^2$, independently of each another, represent an unsaturated or a partially or completely saturated mono- or polycyclic group, a mono- or poly-heterocyclic group, an aralkyl group, or a hetero-alkyl group, which mono- or polycyclic groups or aralkyl or hetero-alkyl groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —C(O)R', —C(S)R', —C(O)OR', —C(S)OR', —C(O)SR', or —C(S)SR';

wherein

R' represents hydrogen, alkyl, alkenyl, alkynyl, cycloalkyl or alkoxy, or a group of the formula NR'''R'''', wherein R''' and R'''', independently of each another, represent hydrogen or alkyl; and $R^3$ and $R^4$, independently of each another, represent alkyl, alkenyl, alkynyl, cycloalkyl, amino, trihalogenmethyl, nitro, cyano, or phenyl, or a group of the formula —OR', —SR', —R'OR'', —R'SR'', —C(O)R', —C(S)R', —C(O)OR', —C(S)OR', —C(O)SR', —C(S)SR', —C(O)NR'(OR''), —C(S)NR'(OR''), —C(O)NR'(SR''), —C(S)NR'(SR''), —CH(CN)$_2$, —C(O)NR'R'', —C(S)NR'R'', —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, CH$_2$OR', CH$_2$SR', —NR'C(O)R'', or —OC(O)R';

wherein

R' and R'', independently of each another, represent hydrogen, alkyl, alkenyl, alkynyl, cycloalkyl or alkoxy, or a group of the formula NR'''R'''', wherein R''' and R'''', independently of each another, represent hydrogen or alkyl;

or $R^3$ and $R^4$ together form an unsaturated or a partially or completely saturated mono- or polycyclic group, or a mono- or poly-heterocyclic group, which mono- or polycyclic groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR';

wherein

R' and R'', independently of each another, represent hydrogen, alkyl, alkenyl, alkynyl, cycloalkyl or alkoxy, or a group of the formula NR'''R'''', wherein R''' and R'''', independently of each another, represent hydrogen or alkyl.

In more preferred embodiment, the chemical compound of the invention is represented by the general formula VI, wherein $R^1$ represents a phenyl group, which may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR';

wherein R' and R'', independently of each another, represent hydrogen, alkyl, alkenyl, alkynyl, cycloalkyl or alkoxy, or a group of the formula NR'''R'''', wherein R''' and R'''', independently of each another, represent hydrogen or alkyl;

$R^2$ represents alkyl, alkenyl, alkynyl, cycloalkyl, amino, trihalogenmethyl, nitro, cyano, or phenyl, or a group of the formula —OR', —SR', —R'OR'', —R'SR'', —C(O)R', —C(S)R', —C(O)OR', —C(S)OR', —C(O)SR', —C(S)SR', —C(O)NR'(OR''), —C(S)NR'(OR''), —C(O)NR'(SR''), —C(S)NR'(SR''), —CH(CN)$_2$, —C(O)NR'R'', —C(S)NR'R'', —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, CH$_2$OR', CH$_2$SR', —NR'C(O)R'', or —OC(O)R';

wherein R' and R'', independently of each another, represent hydrogen, alkyl, alkenyl, alkynyl, cycloalkyl or alkoxy, or a group of the formula NR'''R'''', wherein R''' and R'''', independently of each another, represent hydrogen or alkyl;

$R^3$ and $R^4$, independent of each another, represent alkyl, alkenyl, alkynyl, cycloalkyl, amino, trihalogenmethyl, nitro, cyano, or phenyl, or a group of the formula —OR', —SR', —R'OR'', —R'SR'', —C(O)R', —C(S)R', —C(O)OR', —C(S)OR', —C(O)SR', —C(S)SR', —C(O)NR'(OR''), —C(S)NR'(OR''), —C(O)NR'(SR''), —C(S)NR'(SR''), —CH(CN)$_2$, —C(O)NR'R'', —C(S)NR'R'', —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, CH$_2$OR', CH$_2$SR', —NR'C(O)R'', or —OC(O)R';

wherein R' and R'', independently of each another, represent hydrogen, alkyl, alkenyl, alkynyl, cycloalkyl or alkoxy, or a group of the formula NR'''R'''', wherein R''' and R'''', independently of each another, represent hydrogen or alkyl;

or $R^3$ and $R^4$ together form an unsaturated or a partially or completely saturated mono- or polycyclic group, or a mono- or poly-heterocyclic group, which mono- or polycyclic groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR'', —R'SR'', —C(O)R', —C(S)R', —C(O)OR', —C(S)OR', —C(O)SR', or —C(S)SR';

wherein R' and R'', independently of each another, represent hydrogen, alkyl, alkenyl, alkynyl, cycloalkyl or alkoxy, or a group of the formula NR'''R'''', wherein R''' and R'''', independently of each another, represent hydrogen or alkyl.

In another preferred embodiment, the chemical compound of the invention is represented by the general formula VI, wherein $R^1$ represents a phenyl group, which may optionally be substituted one or more times with substituents selected from the group consisting of halogen, trihalogenmethyl, alkyl, amino, nitro, cyano, or amido, or a group of the formula —R', —OR', —R'OR'', —C(O)R', —C(O)OR', or a phenyl or a phenoxy group, which phenyl or phenoxy groups may optionally be substituted on or more times with substituents selected from the group consisting of halogen, trihalogenmethyl, alkyl, amino, nitro, cyano, or amido, or a group of the formula —R', —OR', —R'OR'', —C(O)R', or —C(O)OR';

wherein R' and R'', independently of each another, represent hydrogen, or alkyl;

$R^2$ represents alkyl, cycloalkyl, trihalogenmethyl, nitro, or cyano, or a group of the formula —OR', —R'OR'', —C(O)R', —C(O)OR', or CH$_2$OR';

wherein R' and R'', independently of each another, represent hydrogen, alkyl, cycloalkyl or alkoxy;

$R^3$ and $R^4$, independent of each another, represent alkyl, cycloalkyl, amino, trihalogenmethyl, nitro, cyano, or phenyl, or a group of the formula —OR', —R'OR", —C(O)R', —C(O)OR', or $CH_2OR'$;

wherein R' and R", independently of each another, represent hydrogen, alkyl, cycloalkyl or alkoxy.

In a third preferred embodiment, the chemical compound of the invention is represented by the general formula VI, wherein $R^1$ represents a phenyl group, which may optionally be substituted one or more times with substituents selected from the group consisting of halogen, trihalogenmethyl, alkyl, amino, nitro, cyano, or amido, or a group of the formula —R', —OR', —R'OR", —C(O)R', —C(O)OR', or a phenyl or a phenoxy group, which phenyl or phenoxy groups may optionally be substituted on or more times with substituents selected from the group consisting of halogen, trihalogenmethyl, alkyl, amino, nitro, cyano, or amido, or a group of the formula —R', —OR', —R'OR", —C(O)R', or —C(O)OR';

wherein R' and R", independently of each another, represent hydrogen, or alkyl;

$R^2$ represents alkyl, cycloalkyl, amino, trihalogenmethyl, nitro, or cyano, or a group of the formula —OR', —R'OR", —C(O)R', —C(O)OR', or $CH_2OR'$;

wherein R' and R", independently of each another, represent hydrogen, alkyl, cycloalkyl or alkoxy;

$R^3$ and $R^4$ together form an unsaturated or a partially or completely saturated mono- or polycyclic group, which mono- or polycyclic groups may optionally be substituted one or more times with substituents selected from the group consisting of halogen, trihalogenmethyl, alkyl, amino, nitro, cyano, or amido, or a group of the formula —R', —OR', —R'OR", —C(O)R', —C(O)OR';

wherein R' and R", independently of each another, represent hydrogen, alkyl, cycloalkyl or alkoxy.

In a most preferred embodiment, the chemical compound of the invention represented by the general formula VI is 2-(3-Phenoxyphenyl)butyronitrile;

2-(2-Chlorophenyl)butyronitrile;

Dicyclopropan(4-chlorophenyl)carbinol;

Ethyl 1-(4-chlorophenyl)cyclopentane-1-carboxylate; or 1-(4-Chlorophenyl)-1-(3-methyl-5-oxadiazolyl)cyclopentane;

or a pharmaceutically acceptable salt or an oxide or a hydrate hereof.

Definition of Substituents

In the context of this invention halogen represents a fluorine, a chlorine, a bromine or an iodine atom. Thus, a trihalogenmethyl group represents e.g. a trifluoromethyl group and a trichloromethyl group.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, and cyclohexyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1,2- or 2,3-propenyl; or 1,2-, 2,3-, or 3,4-butenyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl, 1,2- or 2,3-propynyl, 1,2-, 2,3- or 3,4-butynyl.

In the context of this invention an alkoxy group designates an "alkyl-O—" group, wherein alkyl is as defined above.

In the context of this invention an acyl group designates a carboxy group (—COOH) or an alkylcarbonyl group (alkyl-CO—), wherein alkyl is as defined above. Examples of preferred acyl groups of the invention include carboxy, acetyl, and propionyl.

In the context of this invention an amido group designates a substituent of the formula R'—CO—NH— or R'—CO—N(alkyl)-, wherein R' represents hydrogen or an alkyl group as defined above. Examples of preferred amido groups include formamido, acetamido, and propionamido.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

In the context of this invention a mono- or polycyclic aryl group designates a monocyclic or polycyclic aromatic hydrocarbon group. Examples of preferred aryl groups of the invention include phenyl, naphthyl and anthracenyl.

In the context of this invention an unsaturated mono- or polycyclic group designates mono- or polycyclic aryl group, i.e. monocyclic or polycyclic aromatic hydrocarbon groups. Examples of preferred partially saturated monocyclic groups include cyclopenta-2,4-diene-1-ylidene.

In the context of this invention an aralkyl group designates an aryl group as defined above, which aryl group is attached to an alkyl group as also defined above. Examples of preferred aralkyl groups of the invention include benzyl.

In the context of this invention a mono- or poly-heterocyclic group is a mono- or polycyclic compound, which holds one or more heteroatoms in its ring structure. Preferred heteroatoms include nitrogen (N), oxygen (O), and sulphur (S). One or more of the ring structures may in particular be aromatic (i.e. a heteroaryl), saturated or partially saturated. Preferred heterocyclic monocyclic groups of the invention include 5- and 6-membered heterocyclic monocyclic groups.

Examples of preferred aromatic heterocyclic monocyclic groups of the invention include 1,3,2,4- or 1,3,4,5-dioxadiazolyl, dioxatriazinyl, dioxazinyl, 1,2,3-, 1,2,4-, 1,3,2- or 1,3,4-dioxazolyl, 1,3,2,4- or 1,3,4,5-dithiadiazolyl, dithiatriazinyl, dithiazinyl, 1,2,3-dithiazolyl, furanyt, furazanyl, imidazolyl, isoimidazolyl, 2-isoimidazolyl, isoindazolyl, isothiazolyl, isoxazolyl, 1,2,3-, 1,2,4-, 1,2,5- or 1,3,4-oxadiazolyl, oxatetrazinyl, oxatriazinyl, 1,2,3,4- or 1,2,3,5-oxatriazolyl, oxazolyl, pyrazinyl, pyrazolyl, pyridazinyl, pyridinyl, pyrimidinyl, pyrrolyl (azolyl), 1,2,3,4- or 2,1,3,4-tetrazolyl, thiadiazolyl, thiazolyl, thienyl, 1,2,3-, 1,2,4- or 1,3,5-triazinyl, and 1,2,3-, 1,2,4-, 2,1,3- or 4,1,2-triazolyl. Most preferred heterocyclic monocyclic groups of the invention include furan-2-yl, furan-3-yl, 2-, 4- or 5-imidazolyl, 3-, 4- or 5-isoxazolyl 1-, 2- or 3-pyridinyl, and 1- or 2-thienyl.

Examples of preferred saturated or partially saturated heterocyclic monocyclic groups of the invention include 1,3,5,6,2-dioxadiazinyl, 1,2,3,4,5-, 1,2,3,5,4-dioxadiazolyl, dioxanyl, 1,3-dioxolyl, 1,3,5,6,2-dithiadiazinyl, 1,2,3,4,5- or 1,2,3,5,4-dithiadiazolyl, 2-isoimidazolyl, isopyrrolyl, isotetrazolyl, 1,2,3- or 1,2,4-isotriazolyl, morpholinyl, oxadiazinyl, 1,2,4-, 1,2,6-, 1,3,2-, 1,3,6- or 1,4,2-oxazinyl, piperazinyl, piperidinyl, 1,2-, 1,3- or 1,4-pyranyl, and pyrrolidinyl.

Examples of preferred aromatic heterocyclic polycyclic groups of the invention include acridinyl, benzimidazolyl, 1,2- or 1,4-benzisothiazinyl, 1,2- or 1,4-benzisoxazinyl, benzisoxazole, benzothiazolyl, benzofuranyl, isobenzofuranyl, 2,3-benzopyronyl, 1,2,3,4-benzotetrazinyl, 1,3,4,6-benzotetrazolyl, benzothiazolyl, 1,2,3- or 1,2,4-benzotriazinyl, 1,2,3- or 2,1,3-benzotriazolyl, benzoxadiazolyl, benzoxazolyl, carbazolyl, cinnolinyl, coumarinyl, indazolyl, indolyl, isoindolyl, indolizinyl, purinyl, phenazinyl, phenothiazinyl, phenanthridinyl, phthalazinyl, pteridinyl, quinolinyl, quinoxalinyl, isoquinolinyl, quinazolinyl, quinolizinyl, and xanthrenyl.

Examples of preferred saturated or partially saturated heterocyclic polycyclic groups of the invention include 1,3-benzisodiazolyl, benzomorpholinyl, 1,2- or 1,4-benzopyranyl, 1,3,2-, 1,4,2-, 2,3,1- or 3,1,4-benzoxazinyl, chromanyl, 4H-chromenyl, and indanyl.

In the context of this invention a hetero-alkyl group designates a mono- or poly-heterocyclic group as described above, which heterocyclic group is attached to an alkyl group as also defined above. Examples of preferred heteroalkyl groups of the invention include furfuryl and picolyl.

Pharmaceutically Acceptable Salts

The SK/IK/BK channel modulating agents of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzenesulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

The chemical compound of the invention may be provided in unsolved or solvated forms together with a pharmaceutically acceptable solvents such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolved forms for the purposes of this invention.

Steric Isomers

The SK/IK/BK channel modulating agents of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers. Racemates, and Resolutions*", John Wiley and Sons, New York (1981).

Biological Activity

According to the present invention it has now been found that the isatin derivatives of the invention possess valuable activity as modulators of $SK_{Ca}$, $IK_{Ca}$ and/or $BK_{Ca}$ channels.

The SK/IK/BK channel modulating activity may be monitored using conventional electrophysiological methods such as patch-clamp techniques, or conventional spectroscopic methods such as FLIPR assay (Fluorescence Image Plate Reader; available from Molecular Devices). These methods generally comprises subjecting an $SK_{Ca}$, $IK_{Ca}$ or $BK_{Ca}$ containing cell to the action of the chemical compound of the invention, followed by monitoring the membrane potential of the $SK_{Ca}$, $IK_{Ca}$ or $BK_{Ca}$ containing cell in order to identify changes in the membrane potential caused by the action of the compound of the invention.

In Example 9 the biological activity of the compounds of the invention is demonstrated using electrophysiologic patch-clamp techniques.

Based on their biological activity the compounds of the invention are considered useful for the treatment or alleviation of diseases or conditions responsive to modulation of $SK_{Ca}$, $IK_{Ca}$ and/or BK channels, including diseases or conditions like respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

The compounds of the invention is considered particularly useful for reducing or inhibiting undesired immune-regulatory actions. In a preferred embodiment, therefore, the compounds of the may be used in the treatment or alleviation of a diseases, disorders or condition related to immune dysfunction, or in order to obtain immune suppression in an individual in need herefore.

In a more preferred embodiment, the invention relates to the use of an $IK_{Ca}$ inhibitory compound of the invention in a combination therapy with known immune-suppressants for the treatment or alleviation of a diseases, disorders or condition related to immune dysfunction, or for obtaining immune suppression. Preferred immune-suppressants to combine with the compounds of the invention include Amphotericin, Busulphan, Co-trimoxazole, Chlorambucil, colony stimulating factors, corticosteroids, Cyclophosphamide, Fluconazole, folinic acid, Ganciclovir, antilymphocyte immunoglobulins, normal immunoglobulins, Methotrexate, Methylprednisolone, Octreotide, Oxpentifylline, Tacrolimus, Thalidomide, Zolimomab aritox, and the calcineurin inhibitors (protein phosphatase 2B inhibitors), in particular Cyclosporin and FK506.

Conditions which may benefit from this treatment include, but are not limited to diseases, disorders or conditions such as auto-immune diseases, e.g. Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune haemolysis, Bechet's disease, Boeck's disease, inflammatory bowel disease, Burkiff's lymphoma, Chron's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, auto-immune demyelinating diseases, Dupuytren's contracture, encephalomyelitis, encephalomyelitis allergica, endophthalmia phacoanaphylactica, enteritis allergica, auto-immune enteropathy syndrome, erythema nodosum leprosum, idiopathic facial paralysis, chronic fatigue syndrome, febris rheumatica, giomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminate, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Lesihmania, and immune-suppressed disease states such as viral infections following allograft transplantations, graft vs. Host syndrome, transplant rejection, or AIDS, cancers, chronic active hepatitis diabetes, toxic chock syndrome, food poisoning, and transplant rejection.

Pharmaceutical Compositions

In another aspect the invention provides novel pharmaceutical compositions comprising a therapeutically effective amount of a chemical compound having $SK_{Ca}$, $IK_{Ca}$ or $BK_{Ca}$ modulating activity.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the SK/IK/BK channel modulating agents of the invention, or a pharmaceutically acceptable salt or derivative thereof, together with one or more pharmaceutically acceptable carriers therefor, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis, the SK/IK/BK channel modulating agents of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment or alleviation of diseases or disorders or conditions of living animals, including humans, which diseases, disorders or conditions are responsive to modulation of $SK_{Ca}$, $IK_{Ca}$ and/or $BK_{Ca}$ channels, and which method comprises administering to such a living animal body, including a human, in need thereof an effective amount of a chemical compound of the invention.

In a more preferred embodiment, the disease, disorder or condition is asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples which are not intended to be in any way limiting to the scope of the invention as claimed.

TABLE 1

Substituted Malonic Acid Esters

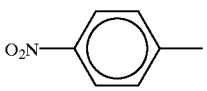

| Entry | A | B | R | $R_1$ | $R_2$ | Mp. | Ex. |
|---|---|---|---|---|---|---|---|
| 1a | — | $CH_2$ | $CO_2Et$ | 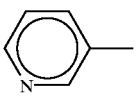 | 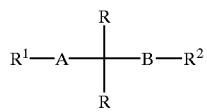 | 159–61.5* | 1, 2 |
| 1b | — | $CH_2$ | $CO_2Et$ | 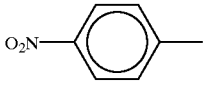 | 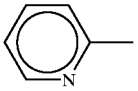 | 161–3* | 1, 2 |

TABLE 1-continued
Substituted Malonic Acid Esters
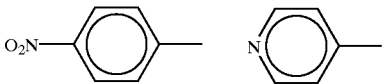
| Entry | A | B | R | R₁ | R₂ | Mp. | Ex. |
|---|---|---|---|---|---|---|---|
| 1c | — | CH₂ | CO₂Et | 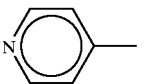 | 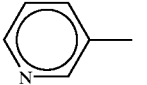 | 174–6* | 1, 2 |
| 1d | — | CH₂ | CO₂Et | Ph | 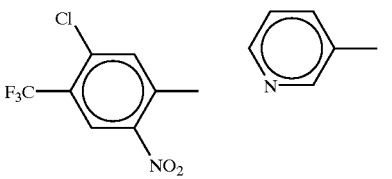 | oil | 1, 2 |
| 1e | — | CH₂ | CO₂Et | 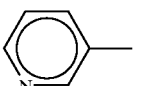 | 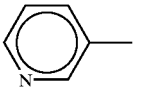 | 167–8* | 1, 2 |
| 1f | CH₂ | CH₂ | CO₂Et | Ph | 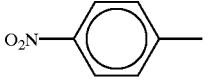 | oil | 1, 2 |
| 1g | — | CH₂ | CO₂Et | Ph | OH | oil | 3 |
| 1h | — | CH₂ | CO₂Et | Ph | Oac | oil | 4 |
| 1i | — | — | CO₂Et | 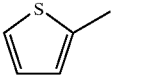 | 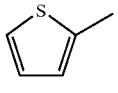 | oil | 1, 9 |
| 1j | — | CH₂ | CO₂Et | 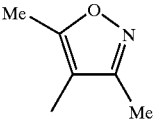 | 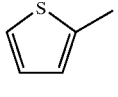 | oil | 1, 9 |
| 1k | — | CH₂ | CO₂Et | 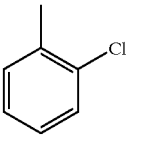 | 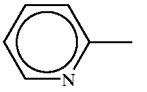 | oil | 1, 9 |
| 1l | — | CH₂ | CO₂Me | OMe | 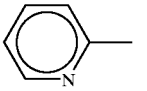 | 67–68 | 1 |
| 1m | — | CH₂ | CO₂Et | NHAc | 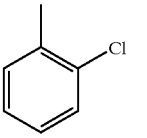 | 91–93 | 1 |
| 1n | — | CH₂ | CO₂Et | NHAc | 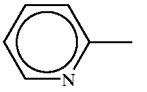 | 89–90 | 1 |

TABLE 1-continued

Substituted Malonic Acid Esters $$R^1-A-\underset{R}{\overset{R}{|}}C-B-R^2$$

| Entry | A | B | R | R₁ | R₂ | Mp. | Ex. |
|---|---|---|---|---|---|---|---|
| 1o | — | CH₂ | CO₂Et | NHAc | 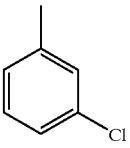 3-Cl-C₆H₄ | 106–107 | 1 |
| 1p | — | CH₂ | CO₂Et | 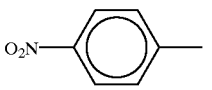 O₂N-C₆H₄ | 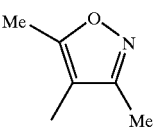 3,4,5-trimethylisoxazole | 94–96 | 1, 2 |
| 1q | CH₂ | CH₂ | CO₂Et | 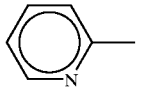 2-pyridyl | 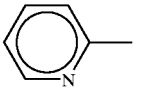 2-pyridyl | 53–55 | 2 |
| 1r | — | CH₂ | CO₂Et | H | 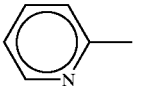 2-pyridyl | 82–84 | 2 |
| 1s | — | CH₂ | CO₂Et | 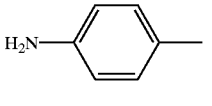 H₂N-C₆H₄ | 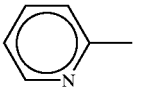 2-pyridyl | 182–184* (decomp.) | 10 |
| 1t | — | CH₂ | CO₂Et | 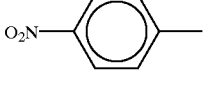 O₂N-C₆H₄ | 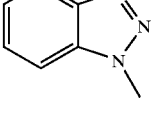 1-methylbenzotriazole | 145–148 | 1 |
| 1u | — | CH₂ | CO₂Et | 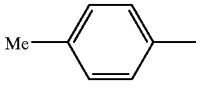 Me-C₆H₄ | 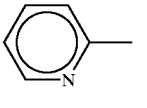 2-pyridyl | oil | 1 |
| 1v | — | CH₂ | CO₂Et | 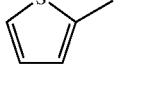 2-thienyl | 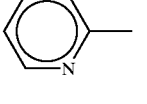 2-pyridyl | 124–126* | 1 |
| 1w | — | CH₂ | CONH₂CN | 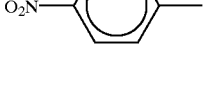 O₂N-C₆H₄ | 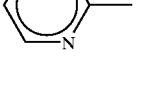 2-pyridyl | 79–81* | 11 |
| 1x | — | CH₂ | CO₂Et | 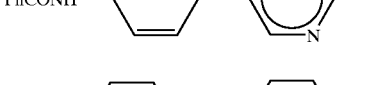 PhCONH-C₆H₄ | 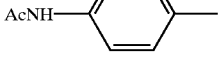 2-pyridyl | 90–95* | 12 |
| 1y | — | CH₂ | CO₂Et | 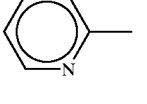 AcNH-C₆H₄ | 2-pyridyl | 66–67* | 12 |

TABLE 1-continued

Substituted Malonic Acid Esters $$R^1-A-\underset{R}{\overset{R}{C}}-B-R^2$$

| Entry | A | B | R | R₁ | R₂ | Mp. | Ex. |
|---|---|---|---|---|---|---|---|
| 1z | — | $CH_2$ | $CO_2Et$ | 2-chlorophenyl | 3-pyridyl | 134–135* | 1, 13 |
| 1za | — | $CH_2$ | $CO_2Et$ | 4-nitrophenyl | 2-bromophenyl | oil | 1, 14 |
| 1zb | — | $CH_2$ | $CO_2$t-Bu | 4-nitrophenyl | 2-pyridyl | 126–129* | 1, 2 |
| 1zc | — | $CH_2$ | $CO_2Et$ | 4-fluorophenyl | 2-pyridyl | 170–172* | 1, 13 |
| 1zd | — | $CH_2$ | $CO_2Et$ | 4-methoxyphenyl | 2-pyridyl | 128–129* | 1, 13 |

*as the hydrochloride.

Example 1

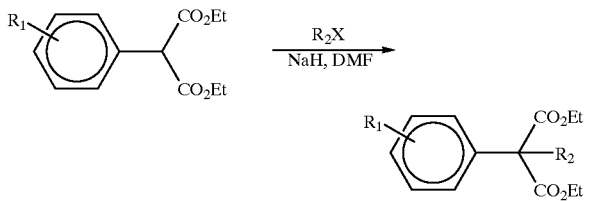

Diethyl 2-(4-fluorophenyl)-2-(3-picolyl)malonate (1a). To a solution of diethyl 2-(4-fluorophenyl)malone (1 g; 3.6 mmol) in anhydrous DMF (10 ml) was added sodium hydride (4.3 mmol, 0.17 g, 60% dispersion in mineral oil). When the evolution of hydrogen had ceased a solution of 3-picolylchloride* (3.6 mmol) in anhydrous DMF (3 ml) was added and the mixture was heated to 80° C. overnight. After cooling four volumes of water was added and the mixture was extracted with ethyl acetate. The organic phase was washed with brine, dried over sodium sulphate and concentrated under reduced pressure. The concentrate was subjected to chromatography on silica gel using a mixture of ethyl acetate and ligroin (1:1) as the eluent. The product precipitated from the eluate as the hydrochloride upon addition of ethereal hydrogen chloride. Yield: 0.32 g (22%). Mp. 159–161.5° C.

*3-Picolychloride was prepared immediately prior to use by liberation from the hydrochloride: 3-picolylchloride, hydrochloride (0.58 g; 3.6 mmol) was dissolved in water (5 ml). Ethyl acetate and saturated aqueous sodium carbonate was added and the phases were separated. The aqueous phase was extracted twice with ethyl acetate and the combined organic phases were dried over sodium sulphate and evaporated to dryness. This residue was dissolved in DMF and used as described above.

The following compounds were prepared analogously:

Diethyl 2-(4-nitrophenyl)-2-(2-picolyl)malonate (1b) from diethyl 2-(4-nitrophenyl)malonate and 2-picolylchloride. Yield: 34%. Mp. 161–163° C.

Diethyl 2-(4-nitrophenyl)-2-(4-picolyl)malonate (1c) from diethyl 2-(4-nitrophenyl)malonate and 4-picolylchloride. Yield: 23%. Mp. 174–176° C.

Diethyl 2-phenyl-2-(3-picolyl)malonate (1d) from diethyl 2-phenylmalonate and 3-picolylchloride. Yield: 58%. M/z: 327 (100%), 281 (43%), 254 (42%), 253 (42%), 235 (51%), 161 (73%).

Diethyl 2-(5-chloro-2-nitro-4-(trifluoromethyl)phenyl)-2-(3-picolyl)malonate (1e) from diethyl 2-(5-chloro-2-nitro-4-(trifluoromethyl)phenyl)malonate and 3-picolylchloride. Yield: 11%. Mp. 167–168° C.

Diethyl 2-benzyl-2-(3-picolyl)malonate (1f) from diethyl 2-benzylmalonate and 3-picolylchloride. Yield: 55% (isolated as the free base). Mp. oil.

Diethyl 2-(2-thienyl)-2-(4-nitrophenyl)malonate (1i) from diethyl 2-(2-thienyl)malonate and 4-fluoro-1-nitrobenzene. THF was used as the solvent. Yield: 7%. Mp. oil.

Diethyl 2-(2-thienyl)-2-(3,5-dimethylisoxazol-4-ylmethyl)malonate (1j) from diethyl 2-(2-thieny)malonate and 3,5-dimethyl-4-(chloromethyl)isoxazole. Yield 39%. Mp. oil.

Diethyl 2-(2-thienyl)-2-(2-chlorobenzyl)malonate (1k) from diethyl 2-(2-thienyl)malonate and 2-chlorobenzylchloride. Yield: 61%. Mp. oil.

Dimethyl 2-methoxy-2-(2-picolyl)malonate (1l) from dimethyl 2-methoxymalonate and 2-picolylchloride. Yield: 56%. Mp. 67–68° C.

Diethyl 2-acetamido-2-(2-picolyl)malonate (1m) from diethyl acetamidomalonate and 2-picolylchloride. Yield: 51%. Mp. 91–93° C.

Diethyl 2-acetamido-2-(2-chlorobenzyl)malonate (1n) from diethyl acetamidomalonate and 2-chlorobenzylchloride. Yield: 56%. Mp. 89–90° C.

Diethyl 2-acetamido-2-(3-chlorobenzyl)malonate (1o) from diethyl acetamidomalonate and 3-chlorobenzylchloride. Yield: 75%. Mp. 106–107° C.

Diethyl 2-(4-nitrophenyl)-2-(3,5-dimethylisoxazol-4-ylmethyl)malonate (1p) from 2-(4-nitropheny(malonate and 3,5-dimethyl-4-(chloromethyl)isoxazole. Yield: 86%. Mp. 94–96° C.

Diethyl 2-(4-nitrophenyl)-2-(benzotriazol-1-ylmethyl)malonate (1q) from 2-(4-nitrophenyl)malonate and 1-(chloromethyl)benzotriazole. Yield: 77%. Mp. 145–148° C.

Diethyl 2-(p-tolyl)-2-(2-picolyl)malonate (1u) from diethyl 2-(p-tolyl)malonate and 2-picolylchloride. Yield: 48%. Mp. oil.

Diethyl 2-(2-thienyl)-2-(2-picolyl)malonate (1v) from diethyl 2-(2-thienyl)malonate 2-picolylchloride. Yield: 45%. Mp. 124–126° C.

Diethyl 2-(2-chlorophenyl)-2-(2-picolyl)malonate (1z) from 2-(2-chlorophenyl)malonate and 2-picolylchloride. Yield: 34%. Mp. 134–135° C.

Diethyl 2-(2-bromobenzyl)-2-(4-nitrophenyl)malonate (1za) from diethyl 2-(2-bromobenzyl)malonate and 4-fluoro-1-nitrobenzene. Yield: 4%. Mp. oil Di-t-butyl 2-(4-nitrophenyl)-2-(2-picolyl)malonate (1zb) from di-t-butyl 2-(4-nitrophenyl)malonate and 2-picolylchloride. Yield: 86%. Mp. 126–129° C.

Diethyl 2-(4-fluorophenyl)-2-(2-picolyl)malonate (1zc) from diethyl 2-(4-fluorophenyl)malonate and 2-picolylchloride. Mp. 170–172° C.

Diethyl 2-(4-methoxy)-2-(2-picolyl)malonate (1zd) from diethyl 2-(4-methoxyphenyl)malonate and 2-picolylchloride. Mp. 128–129° C.

Example 2

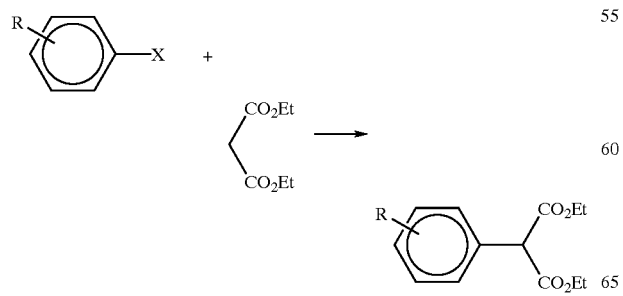

Diethyl 2-(4-nitrophenyl)malonate. To a solution of diethyl malonate (6.1 ml; 40 mmol) in anhydrous THF (60 ml) was added sodium hydride (40 mmol, 1.6 g, 60% dispersion in mineral oil). When the evolution of hydrogen had ceased 1-fluoro-4-nitrobenzene (3.9 ml; 36.3 mmol) was added and the mixture was heated to reflux overnight. The solvent was removed under reduced pressure and the residue was suspended in ethyl acetate. Hydrochloric acid (1 M) was added. The phases were separated and the organic phase was dried over sodium sulphate and evaporated to dryness. The residue was triturated with petroleum ether to afford the product as yellow crystals. Yield: 2.44 g (22%).

The following compounds were prepared analogously:

Diethyl 2-(5-chloro-2-nitro-4-trifluoromethylphenyl)malonate from 2,4-dichloro-5-nitrobenzotrifluoride diethyl malonate. Yield: 54%.

Diethyl 2,2-bis(2-picolyl)malonate (1q), yield: 8%. Mp. 53–55° C.; and diethyl 2-(2-picolyl)malonate (1r), yield: 10%. Mp. 82–84° C.; from diethyl malonate and 2-picolylchloride.

Di-t-butyl 2-(4-nitrophenyl)malonate from di-t-butyl malonate and 4-fluoro-1-nitrobenzene. Yield: 32%.

Example 3

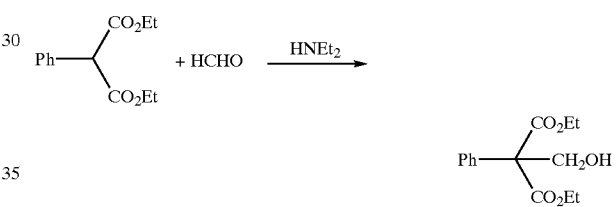

Diethyl 2-phenyl-2-(hydroxymethyl)malonate (1g). To a solution of diethyl 2-phenylmalonate (20 g, 84.6 mmol) and 37% formaline (200 ml) was added diethylamine (8.12 ml; 116 mmol) dropwise at 0° C. The solution was then allowed to stir at ambient temperature for 3 days. The obtained solution was extracted with diethyl ether. The combined organic phases were washed with water, saturated aqueous NaCl-solution, dried over $MgSO_4$, filtered and evaporated. After column chromatography on silica gel eluting first with ligroin (80–100° C.) ethyl acetate 6:1, then 3:1, the product was obtained as a slightly yellowish oil (20.1 g, 89%).

$^{13}C$ nmr ($CDCl_3$, 125.8 MHz): 170.91, 135.77, 129.66, 128.85, 128.54, 128.29, 127.92, 67.50, 65.63, 62.63, 14.33.

Example 4

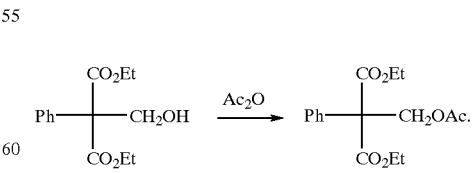

Diethyl 2-phenyl-2-(acetoxymethyl)malonate (1h). Diethyl 2-phenyl-2-hydroxymethyl malonate (612 mg; 2.3 mmol) in dry THF (3 ml) was treated with triethylamine (353 µl; 2.53 mmol), acetic anhydride (240 µl, 2.53 mmol) and a few crystals of 4-dimethylaminopyridine. The obtained solution was stirred for 17 hours and then poured into ice-water followed by extraction with diethyl ether. The combined organic fractions were washed with saturated aqueous NaCl-solution and dried over MgSO$_4$, filtered and evaporated. After column chromatography on silica gel eluting with benzine (80–100° C.) ethyl acetate 3:1 the product was obtained as a yellow oil (340 mg, 47.9%).

$^{13}$C nmr (CDCl$_3$, 25.8 MHz): 170.62, 168.89, 135.19, 128.72, 128.48, 128.30, 66.28, 62.90, 62.43, 21.14, 14.34.

Example 5

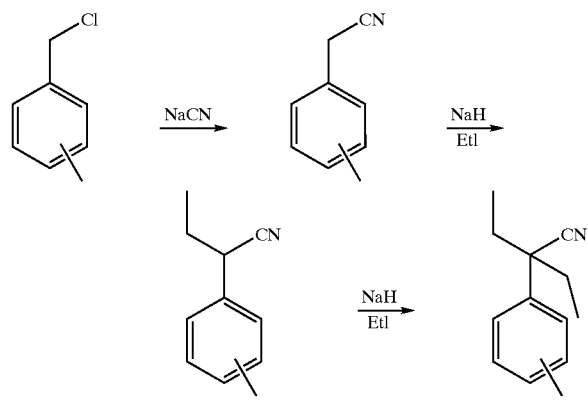

2-Chlorophenylacetonitrile. To a hot (80–90° C.) solution of sodium cyanide (2.3 g; 47 mmol) in water (10 ml), a solution of 2-chlorobenzylchloride (4.9 ml; 39 mmol) in absolute ethanol (5 ml) was added dropwise over 20 minutes. The mixture was stirred at reflux for 3 hours. The cooled mixture was diluted with water and excess cyanide was destroyed by addition of potassium permanganate. The mixture was extracted twice with ethyl acetate. The organic phases were washed with brine, dried over magnesium sulphate and concentrated on a rotary evaporator. The residue was subjected to chromatography on silica gel using a mixture of ethyl acetate and ligroin (1:9 v/v) as the eluent. Yield: 4.5 g (29.8 mmol; 76%).

2-(2-Chlorophenyl)butyronitrile. To a solution of 2-chlorophenylacetonitrile (2.1 g; 13.9 mmol) in anhydrous DMF (10 ml), sodium hydride (15.3 mmol; 0.61 g dispersion in mineral oil) was added in portions under a stream of nitrogen. The resulting mixture was stirred at ambient temperature for one hour, and iodoethane (1.2 ml; 14.6 mmol) was added. After additional stirring at ambient temperature for one hour, the mixture was diluted with four volumes of water and extracted twice with ethyl acetate. The extract was dried over magnesium sulphate and concentrated under reduced pressure. The residue was subjected to chromatography on silica gel using a mixture of ethyl acetate and ligroin (1:4 v/v) as the eluent. Yield: 1.5 g (60%).

The following compounds were prepared in analogy with the above procedure:

2-(2-Chlorophenyl)-2-ethylbutyronitrile was prepared from 2-(2-chlorophenyl)butyronitrile (1.5 g; 8.4 mmol), sodium hydride (0.37 g 60% in mineral oil) and iodoethane (0.67 ml; 8.4 mmol) in anhydrous DMF (10 ml). Yield: 0.2 g (11.5%). M$^+$: 207.

2-(3-Phenoxyphenyl)butyronitrile was prepared from 3-phenoxyphenylacetonitril (1.0 g; 4.79 mmol), sodium hydride (4.79 mmol; 0.19 g 60% in mineral oil) and iodoethane (0.38 ml; 4.79 mmol) in anhydrous DMF (10 ml). Yield: 0.72 g (63%).

2-Ethyl-2-(3-phenoxyphenyl)butyronitrile was prepared from 2-(3-phenoxyphenyl)butyronitrile (0.72 g; 3.0 mmol), sodium hydride (3.0 mmol; 0.12 g 60% in mineral oil) and iodoethane (0.24 ml; 3.0 mmol) in anhydrous DMF (10 ml).

Yield: 0.32 g (40%). M$^+$: 265.

Example 5a

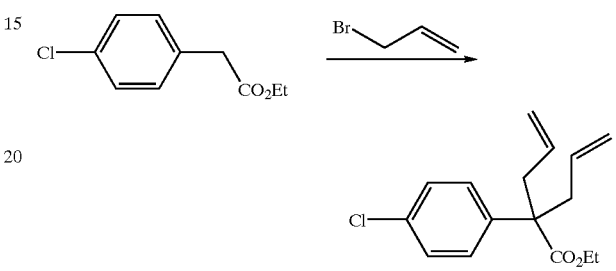

Ethyl 2-(4'-chlorophenyl))-2,2-diallyl-acetate. To a solution of ethyl 2-(4'-chlorophenyl))-acetate (4.0 g; 20.1 mmol) in anhydrous NMP (75 ml) was added 1 eq. sodium hydride (805 mg; 20.1 mmol; 60% suspension). Then 1 eq. allylbromide (2.45 g; 20.1 mmol) was added. After stirring for 1 hour, another equivalent NaH (805 mg; 20.1 mmol; 60% suspension) and a second equivalent allyl-bromide (2.45 g; 20.1 mmol) were added. The obtained mixture was heated to 50° C. for 66 hours. Then it was poured into 400 ml ice-water and extracted with ethyl acetate. The combined organic extracts were washed with water and brine, dried over magnesium sulphate, filtered and evaporated under reduced pressure. Column chromatography using ethyl acetate/ligroin 1:10 as eluent gives the desired compound as a slightly yellowish oil.

Yield: 2.78 g; 50.1%). M/z: 278 (22%), 237 (58%), 205 (40%), 165 (81%), 125 (100%).

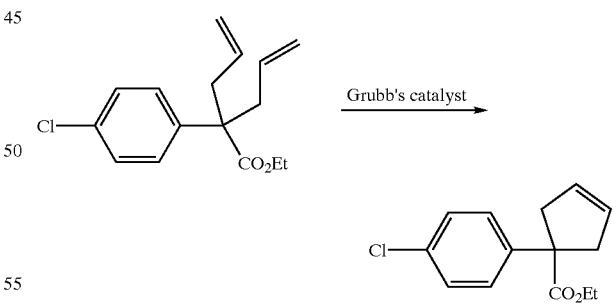

Ethyl 1-(4'-chlorophenyl)cyclopent-3-ene-1-carboxylate. Grubb's catalyst (125 mg; 0.15 mmol; 2.2 mol %) was dissolved in anhydrous toluene (200 ml) under nitrogen giving a wine-red solution. Then ethyl 2-(4'-chlorophenyl))-2,2-diallyl-acetate (1.87 g; 6.71 mmol) in dry toluene (5 ml) was added. After stirring for 20 h the now brownish-black solution was allowed to stir in the presence of air for another 2 hours. The solvent was evaporated under reduced pressure. Column chromatography using benzin/ethylacetate 9:1 then provides the product as a brownish oil. Yield: 1.35 g (80.0%). M/z: 250 (14%), 221 (12%), 177 (100%), 141 (41%).

Example 6

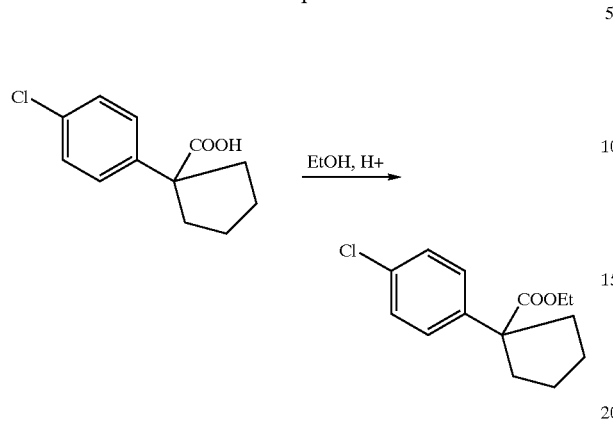

Ethyl 1-(4-chlorophenyl)cyclopentane-1-carboxylate. 1-(4-Chlorophenyl)cyclopentane-1-carboxylic acid (0.5 g; 2.22 mmol) was esterified in ethanol (5 ml) with acid catalysis (10 ml conc. hydrochloric acid) under standard conditions. Yield: 0.44 g, oil (78%). $M^+$: 252.

Example 7

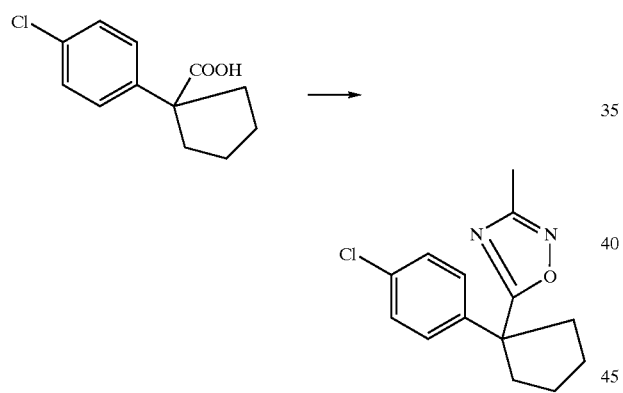

1-(4-Chlorophenyl)-1-(3-methyl-5-oxadiazolyl)cyclopentane. A stirred solution of 1-(4-chlorophenyl)cyclopentane-1-carboxylic acid (1.0 g; 4.45 mmol) in anhydrous THF (10 ml) was heated to reflux. Carbonyldiimidazole (1.08 g; 6.66 mmol) was added and heating was continued overnight. To this hot solution acetamide oxime (0.82 g; 11.1 mmol) was added and heating was continued an additional night. The resulting mixture was cooled and evaporated to dryness. The residue was partitioned between water and ethyl acetate. The organic phase was dried over magnesium sulphate and concentrated under reduced pressure. The concentrate was suspended in toluene (5 ml), a catalytic amount of p-toluenesulphonic acid was added and the mixture was heated to reflux for three hours. After cooling the mixture was decanted and the oily bottom layer was extracted with toluene. The combined decantate and toluene extract were washed with water, dried over magnesium sulphate and evaporated to dryness. The residue was triturated with ligroin to leave the crystalline product (0.31 g; 27%). Mp. 68.7–70.8° C.

Example 7a

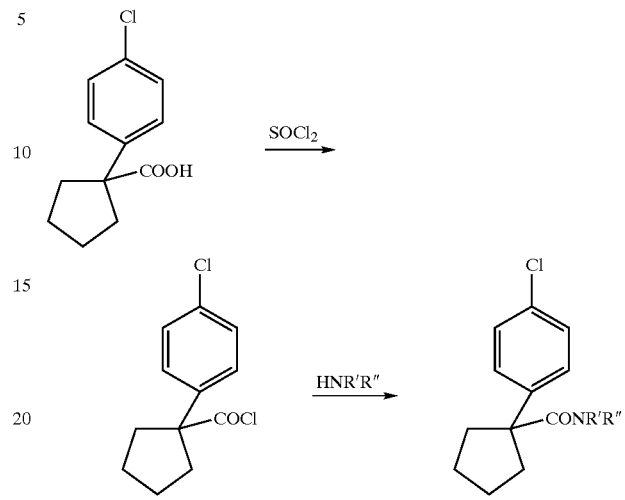

1-(4-chlorophenyl)cyclopentane-1-carboxylic acid chloride was prepared by reflux of 1-(4-chlorophenyl)cyclopentane-1-carboxylic acid in thionyl chloride and subsequent removal of excess thionyl chloride by evaporation. This acid chloride was treated with the appropriate amines in diethyl ether to yield:

N,N-Dimethyl 1-(4-chlorophenyl)cyclopentane-1-carboxamide. Mp. 59–62° C.;

N,N-Diethyl 1-(4-chlorophenyl)cyclopentane-1-carboxamide. Mp. 38–40° C.;

N-Phenyl 1-(4-chlorophenyl)cyclopentane-1-carboxamide. Mp. 127–128° C.

Example 8

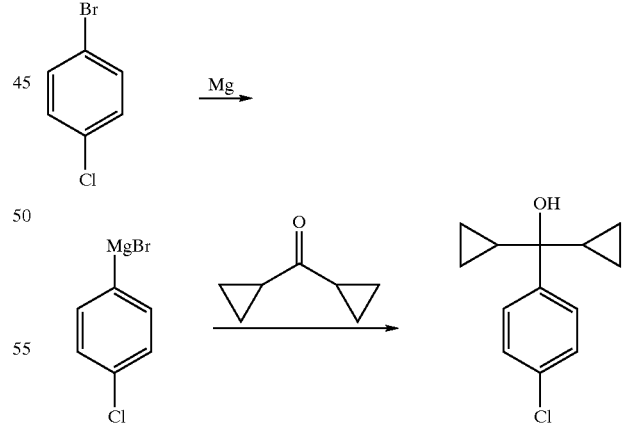

Dicyclopropan(4-chlorophenyl)carbinol. A solution of 4-bromo-1-chlorobenzene (3.47 g; 18.15 mmol) in anhydrous diethyl ether (10 ml) was added dropwise to magnesium turnings (0.44 g; 18.15 mmol) covered with anhydrous diethyl ether (10 ml) in an inert atmosphere at a rate that ensured gentle reflux. Following the addition the mixture was refluxed for additionally 30 minutes. To this mixture a solution of diisopropylketone (2.0 g; 18.15 mmol) in anhydrous diethyl ether (10 ml) was added dropwise and the reaction mixture was left at ambient temperature overnight. Ice-cold, diluted hydrochloric acid was added and the product was extracted with diethyl ether. The organic extract was dried over magnesium sulphate, concentrated under reduced pressure and purified by column chromatography on silica gel using a mixture of ethyl acetate and ligroin (1:9 v/v) as the eluent. This procedure left the pure product (3.3 g; 82%) as an oil. M+ 222.

Example 8a

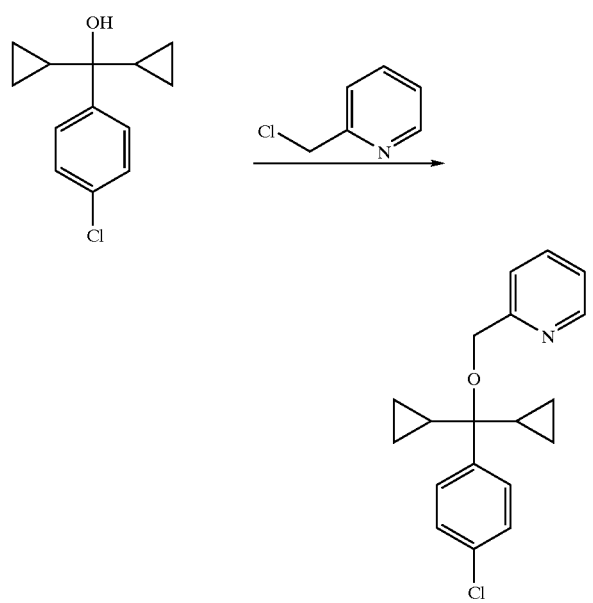

O-(2-picolyl) dicyclopropan(4-chlorophenyl)carbinol. To a solution of 2-picolylchloride, hydrochloride (0.39 g, 3.0 mmol) in DMF (5 ml) was added sodium hydride (0.12 g 60% dispersion in mineral oil). When the evolution of hydrogen had ceased a solution of dicyclopropan(4-chlorophenyl)carbinol (0.67 g, 3.0 mmol) in DMF (5 ml) was added and the mixture was heated to 100° C. for 2 days. The cooled mixture was poured into water and extracted with ethyl acetate. Column chromatographic workup on silica gel using ethyl acetate as the eluent yielded the desired product (40 mg) as an oil.

Example 9

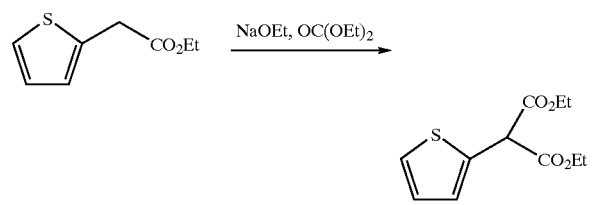

Diethyl 2-(2-thienyl)malonate. A mixture of sodium ethanolate in ethanol (15 ml, 2 M) and anhydrous THF (30 ml) was heated to 60° C. Diethyl carbonate (3.63 ml, 30 mmol) was added and heating was continued for 45 minutes. Ethyl 2-thienylacetate (4.40 ml, 29.4 mmol) was added dropwise and the mixture was refluxed overnight. After cooling the mixture was poured into ice-water and pH was adjusted to approx. 6 by addition of diluted acetic acid. Extraction with ethyl acetate followed by column chromatographic work up yielded the desired product (3.35 g, 47%).

Example 10

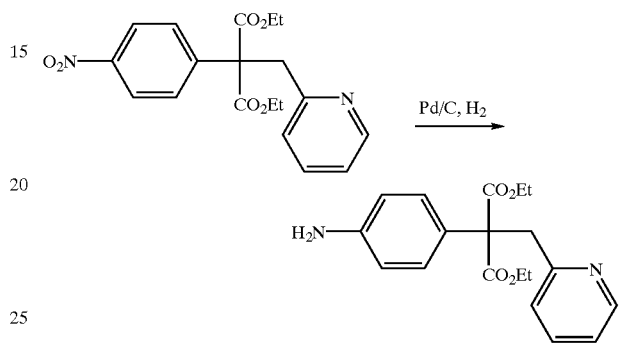

Diethyl 2-(4-aminophenyl)-2-(2-picolyl)malonate (1s). A solution of 1b (1.0 g, 2.69 mmol) in ethanol (20 ml) was hydrogenated at ambient pressure using palladium (0.1 g 5% Pd on activated carbon) as the catalyst until the hydrogen uptake had ceased. After filtration through celite the product was precipitated as the hydrochloride by addition of etheral hydrogenchloride to the filtrate. Filtration left the desired product quantitatively. Mp. 182–184° C. (with decomposition).

Example 11

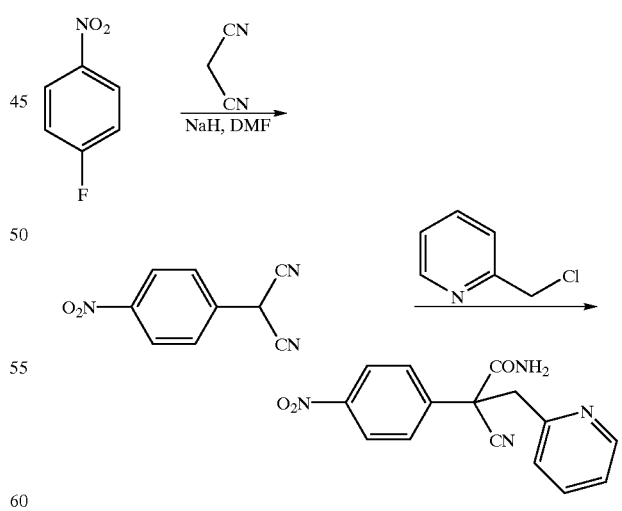

2-(4-nitrophenyl)malononitril (2w). To a solution of malononitril (0.75 g, 11.4 mmol) in DMF was added sodium hydridre (0.28 g 60% dispersion in mineral oil). When the evolution of hydrogen had ceased 4-fluoro1-nitrobenzene (1.0 g, 7.09 mmol) was added and the mixture was heated to 80° C. overnight. After cooling the mixture was poured into a mixture of diethyl ether and petroleum ether and the insoluble oil was washed several times the diethyl ether petroleum ether mixture leaving oily crystals of 2-(4-nitrophenyl)malononitril sodium salt (0.62 g, 47%).

2-Cyano-2-(4-nitrophenyl)-3-(2-pyridyl)propionamide (1w). To a suspension of 2-picolylchloride hydrochloride (0.39 g, 2.38 mmol) in DMF (5 ml) was added sodium hydride (0.1, 60% suspension in mineral oil). When the evolution of hydrogen had ceased 2w (0.5 g, 2.38 mmol) and a catalytic amount of DMAP was added and the mixture was heated to 150° C. for 3 days. The cooled mixture was poured into water and the precipitate was fractionated through a silica gel column using a mixture of ethyl acetate and methanol (9:1 v/v) as the eluent. The product precipitated as the hydrochloride upon addition of etheral hydrogenchloride to the eluate. Yield: 0.19 g (27%). Mp. 79–81° C.

Example 12

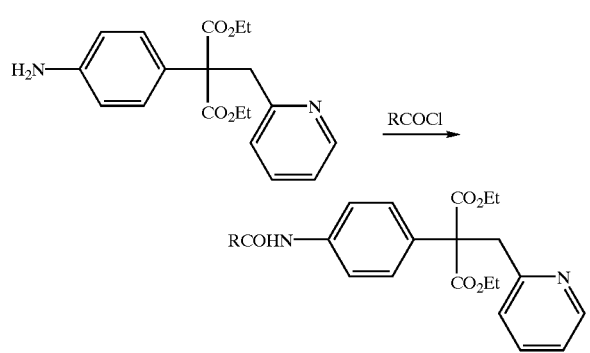

Diethyl 2-(4-(benzoylamino)phenyl)-2-(2-picolyl)malonate (1x). 1s was benzoylated under standard conditions using benzoylchloride in a mixture of THF and dichloromethane as the solvent. The product was isolated as the hydrochloride. Mp. 90–95° C.

Diethyl 2-(4-(acetylamino)phenyl)-2-(2-picolyl)malonate (1 y). 1s was acetylated under standard conditions using acetic anhydride in dichloromethane. The product was isolated as the hydrochloride. Mp.: 66–67° C.

Example 13

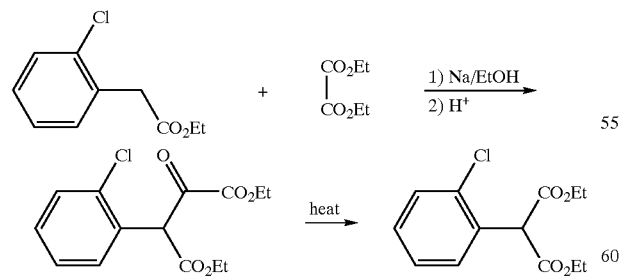

Diethyl 2-(2-chlorophenyl)malonate. A solution of sodium (0.12 g, 5.0 mmol) in anhydrous ethanol (10 ml) was heated to 60° C. Diethyl oxalate (0.68 ml, 5.0 mmol) and 2-chlorophenylacetic acid were added and the mixture was allowed to cool to ambient temperature overnight. The solvent was removed under reduced pressure and the residue was triturated with petroleum ether. This intermediate sodium salt was liberated by addition of diluted sulphuric acid leaving 3-(2-chlorophenyl)oxalacetic acid which was heated slowly to 175° C. under reduced pressure. When the evolution of carbonmonoxide had ceased the cooled product was dissolved in ethyl acetate and eluted through a short silica gel column with ethyl acetate. The eluate was evaporated to dryness to leave the desired product (0.64 g, 47%).

The following compounds were prepared analogously:

Diethyl 2-(4-fluorophenyl)malonate from ethyl 4-fluorophenylacetic acid. Yield: 74%

Diethyl 2-(4-methoxyphenyl)malonate from ethyl 4-methoxyphenylacetic acid. Yield: 71%.

Example 14

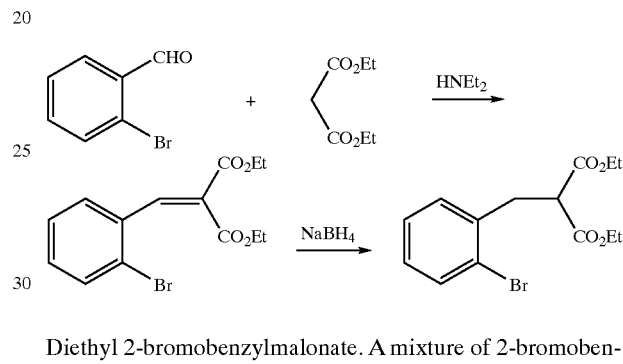

Diethyl 2-bromobenzylmalonate. A mixture of 2-bromobenzaldehyde (2.92 ml, 25.0 mmol), diethyl malonate (38 ml, 25.0 mmol) and diethylamine (2.59 ml, 25.0 mmol) in abs. ethanol (25 ml) was heated to 80° C. overnight. The solvent was removed by evaporation and the residue was partitioned between water and ethyl acetate. The organic phase was purified by column chromatography on silica gel using a mixture of ethyl acetate and ligroin (1:1 v/v) as the eluent.

This intermediate product (5.84 g) was dissolved in abs. ethanol (50 ml) and sodium borohydride (0.68 g, 18.1 mmol) was added in portions. The mixture was stirred for 2 hours at ambient temperature and 4 hours at 60° C., successively. The reaction mixture was left at ambient temperature over the weekend. The mixture was poured into water and rendered acidic by addition of diluted hydrochloric acid. Extraction with ethyl acetate followed by column chromatographic workup on silica gel using a mixture of ethyl acetate and petroleum ether (9:1 v/v) as the eluent left the desired product. Yield: 2.66 g (32% overall).

Example 14a

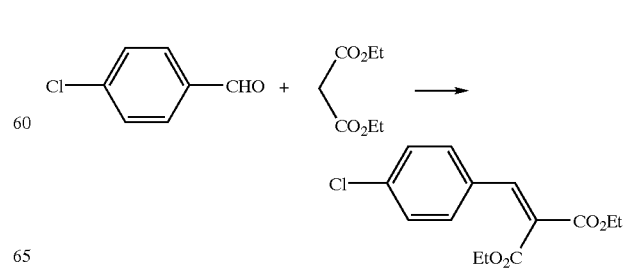

Diethyl 4-chlorobenzylidenemalonate. 4-Chlorobenzaldehyd (26.7 g; 190 mmol), diethyl malonate (30.4 g; 190 mmol), piperidine (1.6 g; 19 mmol) and acetic acid (2.28 g; 38 mmol) were refluxed overnight in toluene using a water separator. Then another portion acetic acid (2.28 g; 38 mmol) and piperidine (1.60 g; 19 mmol) were added and heating continued for another 3 days. After washing with water and brine, drying over magnesium sulphate and evaporation under reduced pressure column chromatography gives the product in an impure form. Destillation of a 25 ml portion then provides the clean material as a clear colourless oil (21.1 g) that solidifies slowly at rt. M/z: 282 (50%), 237 (81%), 203 (43%), 165 (40%), 136 (78%).

Example 15

Electrophysiological Experiments

In this example, the biological activity of the compounds of the invention is demonstrated using electrophysiologic patch-clamp techniques.

Intermediate-conductance $Ca^{2+}$-activated $K^+$ channels (IK channels) have been cloned from human placenta and stably expressed in HEK293 cells. The ionic current through the channels is recorded in the whole-cell mode of the patch-clamp technique.

Stable Expression of IK in HEK293 Cells

Human IK (hIK) was excised from pT3T7 (GenBank Acc. No. N56819) using EcoR I and Not I, and sub-cloned into the mammalian expression vector pNS1Z (NeuroSearch), a custom designed derivative of pcDNA3Zeo (InVitrogen), to give the plasmid construct pNS1Z_hIK.

HEK293 tissue culture cells were grown in DMEM (Dulbecco's Modified Eagle Medium) supplemented with 10% FCS (foetal calf serum) at 37° C. In 5% $CO_2$. One day prior to transfection, $10^6$ cells were plated in a cell culture T25 flask. The following day, cells were transfected using lipofection (20 μL Lipofectamin™, Life Technologies, with 2.5 μg of the plasmid pNS1Z_hIK in a total volume of 540 μL).

The lipofection mixture was overlaid on the cells and incubated at 37° C. for 5 hours. The cells were then rinsed with regular media and grown for 72 hours in DMEM, 10% FCS at 37° C. In 5% $CO_2$.

72 hours post transfection, cells transfected with pNS1Z_hIK were selected in media supplemented with 0.25 mg/ml Zeocin. Single clones were picked and propagated in selection media until sufficient cells for freezing were available. Hereafter the cells were cultured in regular medium without selection agent.

Expression of Functional hIK Channels was Verified by Patch-clamp Measurements.

Whole Cell Recordings

Experiments are carried out on one of several patch-clamp set-ups. Cells plated on coverslips are placed in a 15 μl perfusion chamber (flow rate ~1 ml/min) mounted on a IMT-2 microscope equipped with Nomarski or Hoffmann optics. The microscopes are placed on vibration-free tables in grounded Faraday cages. All experiments are performed at room temperature (20–22° C.). EPC-9 patch-clamp amplifiers (HEKA-electronics, Lambrect, Germany) are connected to Macintosh computers via ITC16 interfaces. Data are stored directly on the hard disk and analysed by the IGOR software (WaveMetrics, Lake Oswega, USA).

The whole-cell configuration of the patch clamp technique is applied. The tip of a borosilicate pipette (resistance 2–4 MΩ) is gently (remote control system) placed on the cell membrane. Light suction results in a giga seal (pipette resistance increases to more than 1 GΩ) and the cell membrane is then ruptured by more powerful suction. Cell capacitance is electronically compensated and the resistance between the pipette and the cell interior (the series resistance, Rs) is measured and compensated for. Usually the cell capacitance ranges from 5 to 20 pF (depending on cell size) and the series resistance is in the range 3 to 6 MΩ. Rs- as well as capacitance compensation are updated during the experiments (before each stimulus).

All experiments with drifting Rs-values are discharged. Leak-subtractions are not performed.

Solutions

All compounds of Table 1 were subjected to this experiment.

The extracellular (bath) solution contains: 144 mM KCl, 2 mM $CaCl_2$, 1 mM $MgCl_2$, 10 mM HEPES (pH=7.4). Test compounds are dissolved in DMSO from stock solution and then diluted to a final concentration of about 10 μM in the extracellular solution. The concentration of $CaCl_2$ is 7.6 mM and that of $MgCl_2$ is 1.2 mM to give calculated free concentrations of 300 nM and 1 mM, respectively.

Quantification

After establishment of the whole-cell configuration, voltage-ramps (usually −100 to +100 mV) are applied to the cell every 5 sec. A stable baseline current is obtained within a period of 100–300 seconds, and the compounds are then added by changing to an extracellular solution containing the compound to be tested. Very little endogenic current (<200 pA at 100 mV, compared to 2–20 nA IK current) are activated under these circumstances in native HEK293 cells.

Results

All compounds tested in this experiment showed activity at a final concentration of about 10 μM, and these compounds therefore are SK/IK/BK channel modulating agents.

The invention claimed is:

1. A malonic acid ester compound of Formula II

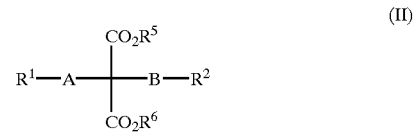

(II)

or a pharmaceutically acceptable salt or a hydrate thereof, wherein,

A is absent; and

B represents a group of the formula —$(CH_2)_n$—, wherein n is 1;

$R^1$ represents a phenyl or a benzyl group, said phenyl and benzyl groups being substituted one or two times with substituents selected from the group consisting of halogen, trihalogenmethyl, nitro, and cyano;

$R^2$ represents a mono-heterocyclic aromatic group selected from the group consisting of pyridinyl, said pyridinyl, being unsubstituted or substituted one or two times with substituents selected from the group consisting of being substituted one or two times with substituents selected from the group consisting of halogen, trihalogenmethyl, alkyl, amino, nitro, cyano, alkoxy and phenyl; and $R^5$ and $R^6$, independently of each another, represents alkyl.

2. The compound according to claim 1, wherein $R^1$ represents a phenyl or a benzyl group, said phenyl and benzyl groups being substituted one or two times with substituents selected from the group consisting of halogen, $CF_3$, CN and nitro.

3. The compound according to claim 2, wherein $R^1$ represents 2, 3 or 4-chlorophenyl; 2, 3 or 4-chlorobenzyl; 2, 3 or 4-fluorophenyl; 2, 3 or 4-bromobenzyl; 2, 3 or 4-bromophenyl; 2, 3 or 4-nitrobenzyl; 2, 3 or 4-trifluoromethylphenyl; 2, 3 or 4-trifluoromethylbenzyl; 2-nitro-4-trifluoromethyl-5-chlorophenyl and/or 2-nitro-4-trifluoromethyl-5-chlorobenzyl.

4. The compound according to claim 2, wherein the mono-heterocyclic group is selected from the group consisting of, and 2-, 3- or 4-pyridinyl.

5. The compound according to claim 2, herein the heteroalkyl group is pyridinyl-methyl.

6. The compound according to claim 1, wherein the chemical compound is

Diethyl 2-(4-fluorophenyl)-2-(pyridin-3-yl-methyl)malonate;

Diethyl 2-(4-nitrophenyl)-2-(pyridin-2-yl-methyl)malonate;

Diethyl 2-(4-nitrophenyl)-2-(pyridin-4-yl-methyl)malonate;

Diethyl 2-(2-chlorophenyl)-2-(pyridin-2-yl-methyl)malonate;

Di-t-butyl 2-(4-nitrophenyl)-2-(pyridin-2-yl-methyl)malonate;

Diethyl 2-(4-fluorophenyl)-2-(pyridin-2-yl-methyl)malonate;

or

Diethyl 2-(4-aminophenyl)-2-(pyridin-2-yl-methyl)malonate;

or a pharmaceutically acceptable salt or a hydrate thereof.

7. The compound according to claim 1, wherein $R^2$ represents a 6-membered mono-heterocyclic group selected from the group consisting of pyridinyl, said 6-membered mono-heterocyclic group being unsubstituted or substituted one or two times with substituents selected from the group consisting of halogen, $CF_3$, CN, and nitro.

* * * * *